US006737541B2

(12) United States Patent
Siedlecki et al.

(10) Patent No.: US 6,737,541 B2
(45) Date of Patent: May 18, 2004

(54) PREPARATION OF NITROGEN MUSTARD DERIVATIVES

(75) Inventors: Paul Stanislaw Siedlecki, Macclesfield (GB); David Michael Glanville Martin, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/169,344

(22) PCT Filed: Jan. 13, 2001

(86) PCT No.: PCT/GB01/00218

§ 371 (c)(1),
(2), (4) Date: Nov. 19, 2002

(87) PCT Pub. No.: WO01/55097

PCT Pub. Date: Aug. 2, 2001

(65) Prior Publication Data

US 2003/0162990 A1 Aug. 28, 2003

(30) Foreign Application Priority Data

Jan. 26, 2000 (GB) ................................................ 0001653

(51) Int. Cl.$^7$ ............................................. C07C 229/00
(52) U.S. Cl. ........................................ 560/19; 564/133
(58) Field of Search ................................. 562/433, 442, 562/443, 561, 563, 565; 560/19, 20, 21, 38; 564/123, 144, 133

(56) References Cited

U.S. PATENT DOCUMENTS 5,405,990 A * 4/1995 Burke et al. ................. 560/134
6,339,070 B1 * 1/2002 Emery et al. ................. 514/44

FOREIGN PATENT DOCUMENTS

WO          200066752       * 11/2000

OTHER PUBLICATIONS

Martin et al.,Preparation of the Key Intermediate in a Novel Synthesis of ZD9063P: The Chemical Component of ADEPT, a Targeted Cytotoxic Therapy, Organic Process Research & Development (2000), 4(4), 259–263.*

* cited by examiner

*Primary Examiner*—Johann Richter
*Assistant Examiner*—Karl Puttlitz
(74) *Attorney, Agent, or Firm*—Ropes & Gray LLP

(57) ABSTRACT

This invention relates to an improved synthesis of 5-(N-[(S)-N-{N,N-bis( 2-chloroethyl)amino}phenoxycarbonyl)-γ-glutamyl]amino)isophthalic acid (also named ZD9063P), a prodrug used in Antibody Directed Enzyme Prodrug Therapy (ADEPT), a targeted cytotoxic cancer therapy. Another aspect of the invention comprises a compound of Formula (I) in which $R^1$ and $R^2$ are chloro, $R^3$ is an alphamethylbenzylamine salt of carboxylic acid, $(R^4)_n$ represents a benzyl protected 3,5-dicarboxylic acid and the asterisked chiral carbon in Formula (I) has S configuration, preferably in crystalline form.

10 Claims, No Drawings

PREPARATION OF NITROGEN MUSTARD DERIVATIVES

CROSS-REFERENCE TO RELATED APPLICATIONS

This application is a national stage filing under 35 U.S.C. 371 of PCT application PCT/GB01/00218, filed Jan. 23, 2001, which claims priority from United Kingdom Application No. 0001653.5, filed Jan. 26, 2000, the specifications of each of which are incorporated by reference herein. PCT Application PCT/GB01/00218 was published under PCT Article 21(2) in English.

The present invention relates to an improved synthesis of 5-(N-[(S)-N-{N,N-bis(2-chloroethyl) amino}phenoxycarbonyl)-γ-glutamyl]amino)isophthalic acid (also named ZD9063P herein), a prodrug used in Antibody Directed Enzyme Prodrug Therapy (ADEPT), a targeted cytotoxic cancer therapy.

The use of cytotoxic drugs is limited by their general toxicity and a highly desirable aim is the targeted delivery of the active cytotoxic agent. A novel approach under development is the dosing of the patient with an antibody/enzyme complex which binds specifically at the site of the tumour. Subsequent treatment with a synthetic compound, the Prodrug, which bears a masked cytotoxic entity and has been specifically designed to be cleaved by the enzyme, delivers the cytotoxic agent, the Drug, at the site of the tumour.

The known synthesis of ZD9063P involved a using a nitrogen mustard, N,N-bis(2-chloroethyl)aminophenol, and being the actual cytotoxic agent and would pose very significant containment problems if used on a manufacturing scale (see U.S. Pat. No. 5,405,990; Example 46). Therefore there was a need for an improved synthetic route, particularly a route more suited to large scale manufacture.

The present invention is based on the discovery of a new, efficient and convergent route to ZD9063P and structurally related prodrugs by converting a readily available starting material to a key intermediate suitable for both chemical and enantiomeric purification. The success of the synthetic approach arose from the use of a catalyst to obtain regiospecific opening of an anhydride ring, incorporation of a reaction at an elevated pressure to avoid a solvent exchange and the development of an improved practical procedure for the deprotection of t-butyl esters.

According to one aspect of the invention there is provided a method of preparation of a compound of Formula I or an $R^4$ deprotected derivative thereof

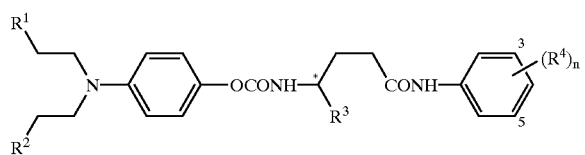

wherein
$R^1$ and $R^2$ independently represent chloro, bromo, iodo or $OSO_2Me$;
$R^3$ represents COOH or a salt of carboxylic acid;
n is 1, 2, 3 or 4;
$R^4$ represents a protected form of COOH, tetrazol-5-yl or $SO_3H$; and
in which the method comprises reacting a compound of Formula II:

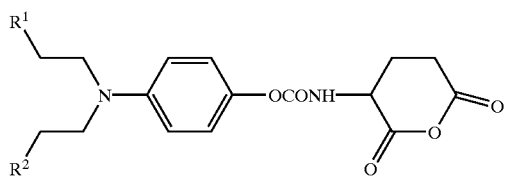

with a compound of Formula III:

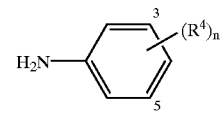

to give a compound of Formula I and optionally further comprising deprotecting $R^4$ and optionally converting the product thus obtained into a pharmaceutically acceptable salt thereof.

$R^1$ and $R^2$ are preferably chloro. $R^3$ is preferably an alphamethylbenzylamine salt of carboxylic acid. $R^4$ is preferably a protected form of COOH, especially COOBn. Preferably n is 2 and especially a 3,5 dicarboxylic acid in protected form is preferred. Preferably the asterisked chiral carbon in Formula I has S configuration.

Preferably the reaction is performed in the presence of a highly nucleophilic but weakly basic amine. Preferably the amine is DMAP (4-dimethylaminopyridine) or 4-pyrrolidinopyridine, especially DMAP. This has the advantage of regioselective opening of the cyclic anhydride ring.

Preferably the reaction is performed at a temperature of −50° to 30°, more preferably −40 to 0°, more preferably −40 to −10° and especially at about −35 to −25°. Preferred temperature ranges have the advantage of giving improved yield of desired reaction products.

According to another aspect of the invention there is provided a method of preparation of a a compound of Formula II which comprises removing the tBu protecting groups from a compound of Formula IV:

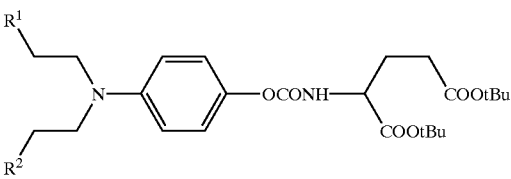

in the presence of methane sulphonic acid followed by cyclisation to the anhydride to give a compound of Formula II. This is advantageous because the de-esterification could be readily achieved by the extended reaction of trifluoroacetic acid but a significant practical problem encountered was the complete removal of the excess trifluoroacetic acid prior to the activation step. A large excess of trifluoroacetic acid is required to displace the equilibrium set up between its t-butyl ester and the corresponding t-butyl ester of the substrate. Complete reaction is normally only achieved by multiple treatments removing volatile substances by distillation, a time-consuming procedure for large scale operation. The t-butyl ester of methanesulphonic acid is unstable and so the corresponding equilibrium can be displaced by the formation of isobutylene which escapes from the system.

According to another aspect of the invention there is provided a method of preparation of a compound of Formula IV in which $R^1$ and $R^2$ are chloro which comprises reacting a compound of Formula V:

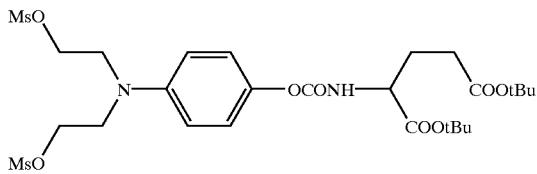

with methane sulphonyl chloride in the presence of methylene chloride in a pressure vessel to give a compound of Formula IV in which $R^1$ and $R^2$ are chloro. This is advantageous for the following reasons. The readily available starting material reacts with methanesulphonyl chloride/ diisopropylethylamine in methylene chloride solution to give an essentially quantitative yield of the corresponding dimesylate. The mesylate groups (also termed "Ms" or "methanesulphonyl" herein) are displaced by the chloride ion present but the reaction is very slow even at reflux. An alternative solvent is not an attractive option as methylene chloride is the most suitable solvent for obtaining an initial solution of starting material, a necessary requisite for a high chemical conversion to the dimesylate. The solvent used must be compatible with the strongly acidic reaction conditions required for removal of the t-butyl groups as the isolation of 10 (for numerically identified compounds, see Schemes below) as a crystalline solid is not easy and it is more convenient to proceed directly with the deprotection stage. In addition, both 10 and 14 contain the nitrogen mustard system, albeit in a less activated form, and handling of such intermediates would cause concern on a production scale. The problem of the slow rate of the displacement reaction at reflux in methylene chloride solution (40° C.) was overcome, without introducing a change to a higher boiling solvent, by operating the reaction under pressure. Complete exchange occurs after 18 hours at 75° C. and the pressure generated in the system, about 2 BarG, is entirely consistent with operation in a standard production plant.

According to another aspect of the invention there is provided a compound of Formula I in which $R^1$ and $R^2$ are chloro, $R^3$ is an alphamethylbenzylamine salt of carboxylic acid and $(R^4)_n$ represents a benzyl protected 3,5-dicarboxylic acid. Preferably the compound is in crystalline form.

Another aspect of the invention comprises a compound of Formula I

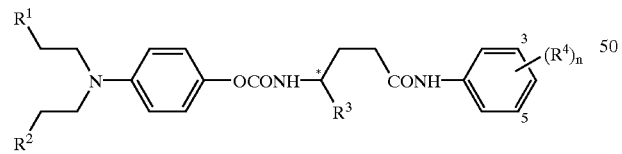

in which $R^1$ and $R^2$ are chloro, $R^3$ is an alphamethylbenzylamine salt of carboxylic acid, $(R^4)_n$ represents a benzyl protected 3,5-dicarboxylic acid and the asterisked chiral carbon in Formula I has S configuration. Preferably the compound is in crystalline form wherein said alphamethylbenzylamine is in enantiomerically pure (R)- or (S)- configuration.

The crystalline form of this compound gives the advantage of ease of handling during manufacture, particularly at large scale.

Explanation of the discovery of the advantageous synthetic route is set out below. A molecule 8, possessing the same basic aryl urethane derivative of (S)-glutamic acid as ZD9063P, was available.
(Scheme 1)

The two key transformations required are the conversion of the hydroxyl groups to chloro groups and the regioselective coupling of the dibenzyl ester of 5-aminoisophthalic acid with the glutamic acid residue giving a compound 9 which can be converted to ZD9063P by catalytic hydrogenation. The key decision is the order in which the chlorination reaction and the introduction of the dibenzyl ester of 5-aminoisophthalic acid moiety are carried out.
(Scheme 2)

Initially, the partial hydrolyses of 8 and of its dichloroanalogue 10 were investigated to provide differentially protected derivatives of glutamic acid. Trifluoroacetic acid selectively cleaved the less hindered ester group but it was not possible to obtain solution yields of the desired regioisomer of greater than about 50% because further de-esterification continually occurred.[i]

The physical characteristics of the chlorinated species as well as the desire to avoid the conversion of the hydroxyl group to the chloro group at a late stage in the synthesis suggested that a dichloro derivative should be chosen as the key starting material for coupling with the dibenzyl ester of 5-aminoisophthalic acid. In addition, approaches based on the opening of the corresponding cyclic anhydride were considered to be more selective than activation of the acyclic system with, for example, a chloroformate ester.

Control of the regioselective opening of anhydrides of glutamic acid derivatives by methanol in the presence of triethylamine containing varying amounts of DMAP has been described. The ratio of regioisomers is reversed from about 1:7 to about 7:1 α/γ by the addition of DMAP.[ii]

Regioselective opening of the anhydrides of phthaloyl derivatives of glutamic acid with amines has been described leading to the γ-isomer and specific reference was made to the opening of the anhydrides of urethane derivatives of the anhydride of glutamic acid with ammonia leading to predominantly the α-isomer.[iii] The regioselectivity of reaction with amines has also been controlled in urethane derivatives of glutamic and aspartic acid anhydrides by choice of reaction solvent.[iv,v,vi] No examples in which DMAP affected the regioselectivity of nucleophilic attack by amines on derivatives of the cyclic anhydrides of glutamic acid have been found.

The invention will now be illustrated by the following non-limiting Examples in which:

Scheme 1 shows synthesis of compound 8 in which a=TMS-Cl, b=4-nitrophenol chloroformate, c=esterification, d=reduction, e=hydroxyethylation Scheme 2 shows options for key transformations in which the bold arrows show the route developed with key intermediates and the dotted arrows show alternative route options with possible intermediates Scheme 3 shows a model experiment Scheme 4 shows a new synthetic route to ZD9063P in which a=MsCl/Hunig's base, b=heat Reagents were purchased from standard suppliers.

NMR spectra were run at 270 MHz (proton) and at 67.7 MHz (carbon) in $d_6$-DMSO or $d_6$-DMSO/TFA solution and are reported in parts per million down field from internal TMS. The signals assigned to TFA (159.0, q, J=60.9 Hz, 115.3, q, J=440 Hz) are omitted from the description of the $^{13}C$ spectrum for each compound.

HPLC analyses were conducted using a HiChrome™ RPB column, solvent system acetonitrile/water/TFA 640/360/1 (v/v/v), flow rate 1 or 2 mL/min and detection at 254λ.

EXAMPLE 1

Model Studies

Derivatives of glutamic acid were used as mechanistic probes to investigate the reaction of anhydrides with the dibenzylester of 5-aminoisophthalic acid.

CBZ-Glutamic acid (CBZ=benzyloxycarbonyl) was converted by DCC (DCC or DCCI=dicyclohexylcarbodiimide) to its cyclic anhydride which was reacted with the p-toluenesulphonate salt of the dibenzylester of 5-aminoisophthalic acid in the presence of an excess of a tertiary amine. Two products were seen in the reactions involving triethylamine and 4-methylmorpholine whereas, completely unexpectedly, a single product resulted when DMAP was used as the base. The compounds were isolated and shown to be 11 and 12, the regioisomers from the opening of the anhydride ring system.[vii]

(Scheme 3)

The single compound formed in the DMAP catalysed reaction corresponded to the more polar regioisomer 12 which possesses the ZD9063P substitution pattern. This key observation means that the basic carbon skeleton of ZD9063P can be assembled without the need for an expensive, differentially protected, glutamic acid derivative.

Racemisation of the chiral centre of the glutamic acid residue is a possible problem with the base catalysed opening of the anhydride ring. The proposed reaction was modelled using the (−)-menthyloxycarbonyl derivative of (R)-glutamic acid because an enantiomeric analytical method for 9 was not initially available. The corresponding anhydride was reacted with the dibenzylester of 5-aminoisophthalic acid in the presence of various tertiary amines and the following results obtained.[viii] [ix]

Results of Opening the Anhydride under Various Conditions (% Yields)

| Base | Desired product | Glutamic acid enantiomer of desired product | Regio-isomer | Glutamic acid enantiomer of regioisomer |
|---|---|---|---|---|
| 4-Methylmorpholine | 50 | 0 | 50 | 0 |
| Pyridine | 50 | 0 | 50 | 0 |
| Triethylamine | 25 | 25 | 25 | 25 |
| No additional base | 15 | 0 | 85 | |
| 4-Pyrrolidino-pyridine | 82 | 16 | 2 | 0 |
| DMAP (at +20° C.) | 88 | 8 | 4 | 0 |
| DMAP (at −30° C.) | 96 | 2 | 2 | 0 |

The results demonstrate that a highly nucleophilic but weakly basic amine possesses the desired catalytic activity for the desired regioselective opening of the cyclic anhydride of a glutamic acid derivative by the dibenzyl ester of 5-aminoisophthalic acid.

EXAMPLE 2

Development of the Manufacturing Route

With the information from the modelling studies, the conversion of 8 to the desired cyclic anhydride was then reinvestigated with a high degree of confidence that the approach would ultimately lead to a practical manufacturing process for ZD9063P.

(Scheme 4)

The readily available starting material 8 reacts with methanesulphonyl chloride/diisopropylethylamine in methylene chloride solution to give an essentially quantitative yield of the corresponding dimesylate. The mesylate groups are displaced by the chloride ion present to give 10 but the reaction is very slow even at reflux. An alternative solvent is not an attractive option as methylene chloride is the most suitable solvent for obtaining an initial solution of 8, a necessary requisite for a high chemical conversion to the dimesylate. The solvent used must be compatible with the strongly acidic reaction conditions required for removal of the t-butyl groups as the isolation of 10 as a crystalline solid is not easy and it is more convenient to proceed directly with the deprotection stage. In addition, both 10 and 14 contain the nitrogen mustard system, albeit in a less activated form, and handling of such intermediates would cause concern on a production scale.

The problem of the slow rate of the displacement reaction at reflux in methylene chloride solution (40° C.) was overcome, without introducing a change to a higher boiling solvent, by operating the reaction under pressure. Complete exchange occurs after 18 hours at 75° C. and the pressure generated in the system, about 2 BarG, is entirely consistent with operation in a standard production plant.

The de-esterification of 10 could be readily achieved by the extended reaction of trifluoroacetic acid but a significant practical problem encountered was the complete removal of the excess trifluoroacetic acid prior to the activation step. A large excess of trifluoroacetic acid is required to displace the equilibrium set up between its t-butyl ester and the corresponding t-butyl ester of the substrate. Complete reaction is normally only achieved by multiple treatments removing volatile substances by distillation, a time-consuming procedure for large scale operation. The t-butyl ester of methanesulphonic acid is unstable and so the corresponding equilibrium can be displaced by the formation of isobutylene which escapes from the system.[x] In this way, complete deprotection of 10 to 14 is achieved using only 0.75 mole equivalents of methane sulphonic acid (18 h at 40° C.). Practical problems arose because the product precipitated as an oily solid in the presence of methane sulphonic acid. However, neutralisation of the added methane sulphonic acid with an equivalent of DMAP successfully overcame the problem giving a solution with a 'pH' suitable for cyclisation to the anhydride with DCC.

The corresponding anhydride 15 of 14 reacts at −30° C. with the dibenzylester of 5-aminoisophthalic acid in the presence of one equivalent of DMAP. The reaction is largely complete within two hours.[xi]

Although it is possible to isolate the free acid form of 9 from the reaction mixture after work-up by crystallisation of the evaporated residue from an ethyl acetate/cyclohexane solvent mixture, it was simpler to isolate the Salt 16 formed with (S)-α-methylbenzylamine directly from a mixture of methylene chloride and acetonitrile. Formation of the salt gave considerable purification as well as an opportunity for any necessary subsequent enantiomeric enrichment.[xii]

The structure of 16 has been correlated with ZD9063P by conversion to the corresponding free acid followed by removal of the benzyl groups by catalytic hydrogenation. The resulting tri-acid was identical to an authentic sample of ZD9063P by $^1$H and $^{13}$C NMR and HPLC.[xiii]

In conclusion, we have developed a new, efficient and convergent route to ZD9063P by converting a readily available starting material to a key intermediate suitable for both chemical and enantiomeric purification. The success of the synthetic approach arose from the use of a catalyst to obtain regiospecific opening of an anhydride ring, incorporation of a reaction at an elevated pressure to avoid a solvent exchange and the development of an improved practical procedure for the deprotection of t-butyl esters

EXAMPLE 3
(S)-(α)-Methylbenzylamine salt of the dibenzyl ester of 5-(N-[(S)-N-{N,N-bis(2-chloroethyl) amino}phenoxycarbonyl)-γ-glutamyl]amino)isophthalic acid. (16)

A solution of 8 (193 g, 0.40 mole) and N,N-diisopropylethylamine (124 g, 167 mL, 0.96 mole) in dichloromethane (1.5 L) was protected from atmospheric moisture and stirred at 0° C. Methane sulphonyl chloride (101 g, 68 mL, 0.878 mole) was added at such a rate so that the reaction temperature remained between 0–5° C. A wash of methylene chloride (200 mL) was added via the dropping funnel. Analysis by HPLC showed greater than 97% AN conversion to the corresponding dimesylate after 2 h.[xiv] The solution was transferred to an autoclave, methylene chloride (460 mL) added and the solution agitated and heated in a sealed vessel for 18 h (jacket temperature 75° C., pressure generated 1.6 BarG). Analysis by HPLC showed a 97% AN conversion to 10. A sample was isolated by chromatography for characterisation.

$^1$H NMR 7.95 (d, J=10 Hz, 1H), 6.94, (d, J=10 Hz, 2H), 6.72 (d, J=10 Hz, 2H), 4.0–3.9, (m, 1H), 3.73 (s, 8H), 2.4–2.3 (m, 2H), 2.0–1.9 (m,1H), 1.9–1.75 (m, 1H), 1.42 (s, 18H)

The cooled reaction mixture was washed with water (570 mL), aqueous citric acid solution (570 mL of 20% w/v) and water (570 mL). The final two separations emulsified slightly. The solution was passed through Whatman 1PS™ filter paper to remove extraneous water. Methanesulphonic acid (57.7 g, 38.9 mL, 0.60 mol) was added and the solution stirred and distilled and one litre of distillate collected. Methylene chloride (1.0 L) was added, the mixture heated and one litre of distillate collected. Further methylene chloride (0.7 L) was added and the mixture heated at reflux for 18 h to give an oily mixture. Analysis of the supernatant solution showed the absence of significant quantities of 13 and any intermediate mono esters. A solution of DMAP (70.8 g, 0.58 mol) in methylene chloride (200 mL) was added slowly. The oil dissolved to give a dark solution and analysis by HPLC showed >95% AN conversion to the desired product, 14, present as a salt with DMAP.

The methylene chloride solution of 14 was inerted by a stream of nitrogen and a solution of DCCI (88.3 g, 0.428 mol) in methylene chloride (220 mL) added over about 1 h maintaining a temperature of 5–10° C. After a further hour, analysis by HPLC showed essentially complete conversion of 14 to the corresponding anhydride 15. The solution was cooled to −50° C. and a solution of DMAP (48.8 g, 0.40 mol) in methylene chloride 200 mL) followed by a solution of the dibenzylester of 5-aminoisophthalic acid (144 g, 0.40 mol) in methylene chloride(800 mL), the temperature being maintained throughout at −50° C. Periodic analysis of the reaction mixture showed it to be essentially complete after 3 h and it was allowed to reach ambient temperature over night. Water (2.5 L) was added, the mixture stirred for 1 h, filtered to remove precipitated N,N$^1$-dicyclohexylurea and the phases separated. The organic phase was washed with aqueous citric acid (2 L of 10% w/v) and water (2 L). The organic solution was filtered through Whatman 1PS™ filter paper to remove adventitious water and divided into two portions of 1.38 L.

One portion was distilled to half volume at atmospheric pressure, diluted with acetonitrile (1.3 L) and stirred at 40° C. whilst a solution of (S)-α-methyl benzylamine (24.2 g, 0.20 mol) in acetonitrile (80 mL) was added. Crystallisation commenced quickly and the slurry was allowed to cool to ambient temperature over 2–3 h. The product was filtered, washed with (2×100 mL methylene chloride/acetonitrile 1/2 v/v) and dried at 30° C. The weight of product 16 was 134 g, 0.154 mol. (76.9% from 8).

EXAMPLE 4
Recrystallisation of the (α)-Methylbenzylamine salt of the dibenzyl ester of 5-(N-[(S)-N-{N,N-bis(2-chloroethyl) amino}phenoxycarbonyl)-γ-glutamyl]amino)isophthalic acid. (16)

The salt 16 (20.0 g, 22.9 mmol) was dissolved in acetonitrile (700 mL) at reflux and cooled to 20° C. The crystalline product was filtered, washed with acetonitrile (100 mL) and dried at 50° C. Yield 14.6 g, 16.7 mmole (73.0% yield)

$^1$H NMR 10.68 (s, 1H), 8.54 (s, 2H), 8.18 (s, 1H), 7.90 (d, J=10 Hz, 1H), 7.52–7.23 (m, 15H), 6.90 (d, J=10 Hz, 2H), 6.68 (d, J=10 Hz, 2H), 5.38 (s, 4H), 4.28 (q, J=10 Hz, 1H), 3.85–3.75 (m, 1H), 3.70 (s, 8H), 2.48–2.37 (m, 2H), 2.20–2.00 (m, 1H), 2.00–1.98 (m, 1H), 1.44 (d, J=10 Hz, 3H)

$^{13}$C 173.8, 171.5, 165.1, 155.2, 144.1, 142.5, 140.6, 139.5, 136.2, 130.8, 129.0, 128.9, 128.8, 128.5, 128.4, 127.0, 124.5, 124.0, 122.9, 67.0, 53.8, 52.8, 50.5, 41.2, 33.1, 26.7, 20.8 Calc for $C_{46}H_{48}N_4O_9Cl_2$: C, 63.37; H, 5.55; N, 6.43, Cl, 8.13. Found: C, 63.34; H, 5.52; N, 6.41, Cl, 8.13.

Quantitative analysis by $^1$H NMR showed the strength to be 100% relative to an internal standard of maleic acid. Additionally, although quantitative analysis by HPLC showed that recrystallisation increased the strength of the product by only 1–2%, comparison of the $^1$H spectra showed that low levels of structurally unrelated aliphatic components had been removed.

EXAMPLE 5
Dibenzyl ester of 5-(N-[(S)-N-{N,N-bis(2-chloroethyl) amino}phenoxycarbonyl)-γ-glutamyl]amino)isophthalic acid. (9)

The above salt 16 (5.0 g, 5.74 mmol) was partitioned between ethyl acetate (150 mL) and an aqueous solution of citric acid (100 mL of 20% w/v). The resulting organic phase was re-washed with an aqueous solution of citric acid (50 mL of 20% w/v) followed by water (3×50 mL). The organic phase was filtered through Whatman 1PS™ filter paper and the solvent removed under reduced pressure to give the desired product 9 as an amorphous foam. Yield 4.0 g, 5.34 mmol (93% yield)

$^1$H NMR 10.5, (s, 1H), 8.60, (s, 2H), 8.28 (s, 1H), 8.00 (d, J=10 Hz, 1H), 7.5–7.3 (m, 10H), 6.94, (d, J=10 Hz, 2H), 6.72 (J=10 Hz, 2H), 5.38 (s, 4H), 4.2–4.1, (m, 1H), 3.73 (s, 8H), 2.68–2.50 (m, coincides with signal from d$^6$-DMSO) 2.62–2.50 (m, 2H), 2.32–2.15 (m, 1H), 2.1–1.9 (m, 1H)

$^{13}$C NMR 173.9, 171.8, 165.1, 155.5, 144.1, 142.5, 140.8, 136.1, 131.2, 128.8, 128.5, 128.2, 124.7, 124.4, 123.0, 112.6, 67.0, 53.8, 53.0, 41.6, 33.0, 27.0

Analysis showed the presence of less than 1% of the (R)-enantiomer.[xv]

EXAMPLE 6
5-(N-[(S)-N-{N,N-bis(2-chloroethyl) amino}phenoxycarbonyl)-γ-glutamyl]amino)isophthalic acid. (ZD9063P)

A sample of 10% palladium/carbon (200 mg) was slurry washed with redistilled THF (20 mL) and transferred to a flask. A solution of 9 (0.30 g, 0.4 mmol) in redistilled THF (50 mL) was added. The slurry was hydrogenated at ambient temperature and pressure. After 18 hours, when removal of the protecting groups was complete, the slurry was diluted with redistilled THF (10 mL) and the catalyst removed by filtration. The solvents were removed under vacuum to leave the product as an amorphous solid, Yield 0.18 g, 0.315 mmol (78.9% yield)

¹H NMR^{xvi} 10.40, (s, 1H), 8.50, (s, 2H), 8.20, (s, 1H), 8.00 (d, J=10 Hz, 1H), 7.00 (d, J=10 Hz, 2H), 6.75 (d, J=10 Hz, 2H), 4.23–4.08 (m, 1H), 3.73, (s, 8H), 2.65–2.52 (m) overlaps with the $d_6$-DMSO signal, 2.35, (m, 1H), 2.10–1.95, (m,1H)
¹³C NMR 173.9, 171.2, 167.2, 155.3, 144.1, 142.6, 140.2, 132.2, 125.2, 124.2, 122.8, 113.0, 54.2, 53.3, 41.7, 33.2, 27.2
-continued
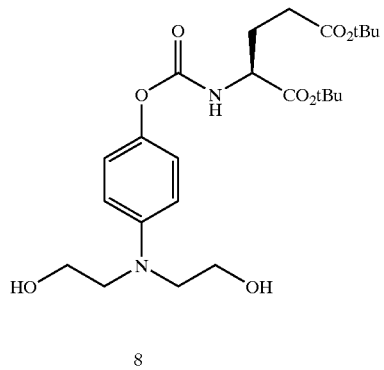
8
Scheme 1
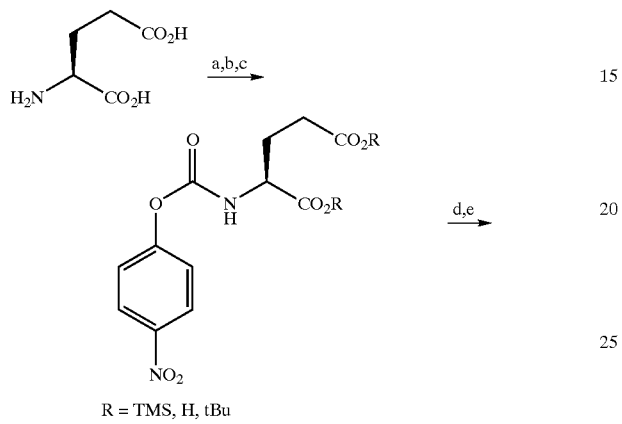
R = TMS, H, tBu
Scheme 2
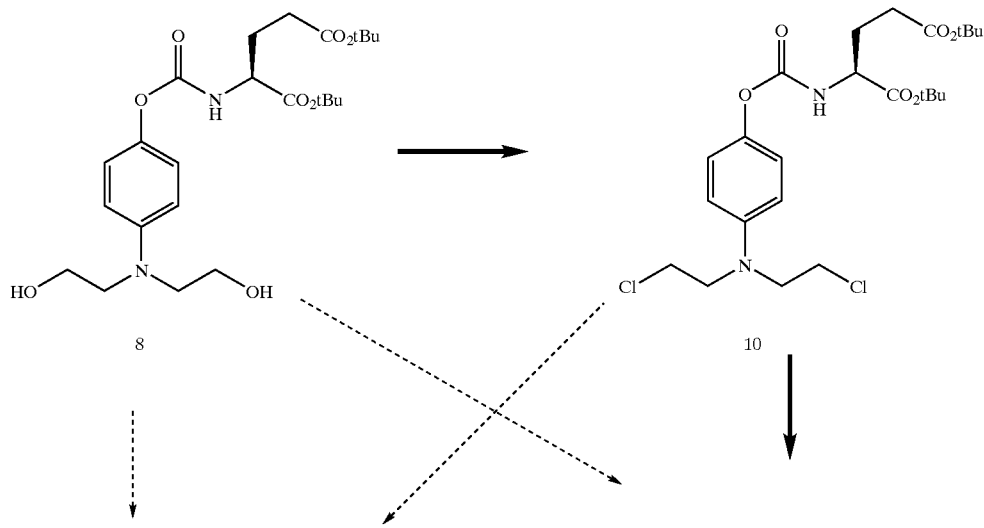

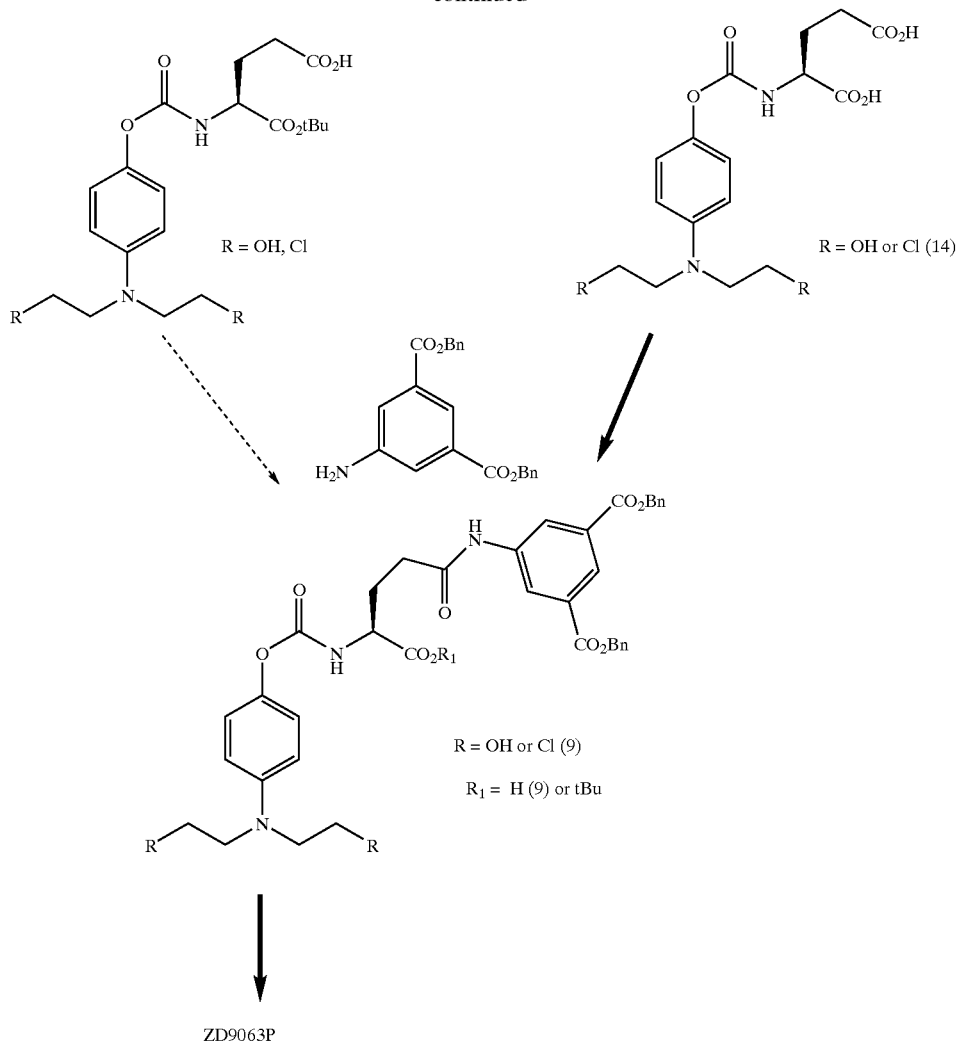
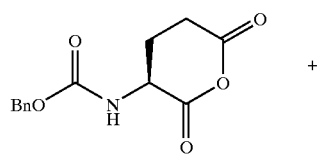
Scheme 3
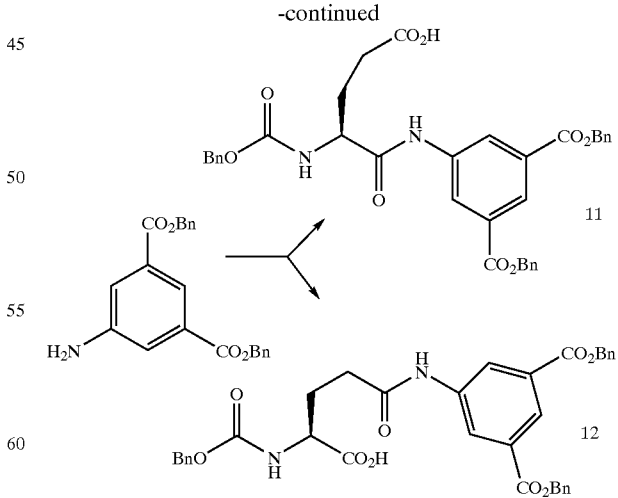

Scheme 4

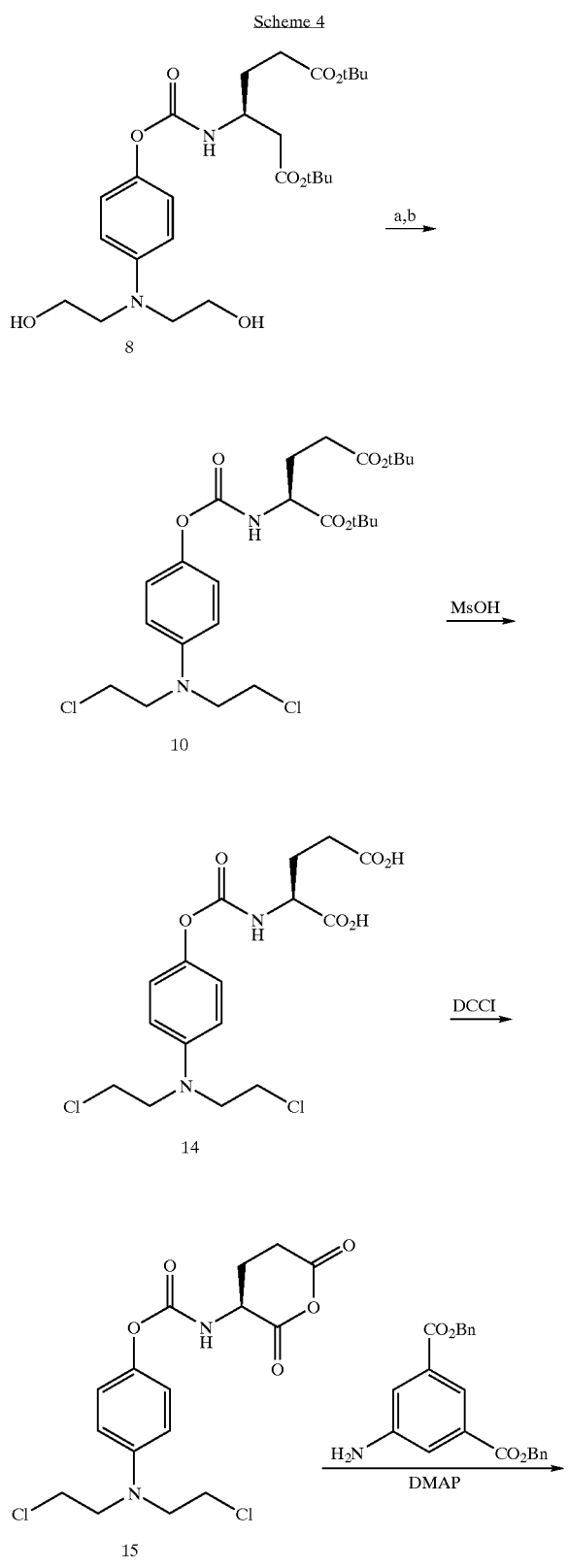

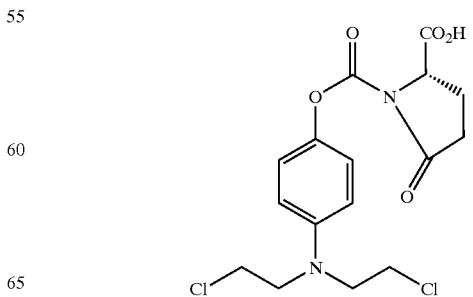

R = Bn, (alpha methylbenzylamine salt
R = H, ZD9063P

[i] The structure of the major regioisomer of the mixture was assigned by comparison of the chemical shifts in the NMR spectra of the protons adjacent to the carbonyl groups in the glutamic acid residue in the acid and salt forms of the product. Formation of the ammonium salt resulted in an up-field shift of approximately 0.2 ppm in the position of the methylene protons thus showing them to be adjacent to a carboxylic acid group and not an ester function.

[ii] Jouin, P.; Castro, B.; Zeggaf, C.; Pantaloni, A.; Senet, J. P.; Lecolier, S.; Sennyey, G, *Tetrahedron Lett*. 1987, 28, 1665

[iii] Sheehan, J. C.; Bolhofer, W. A.; *J. Am. Chem. Soc* 1950, 72, 2469

[iv] Cristea, I.; Mager, S.; Batiu, C.; Plé, G. *Rev. Roum. Chim.,* 1994, 39(12), 1435

[v] Huang X.; Luo X.; Roupioz Y.; Keillor J. W. *J. Org. Chem.* 1997, 62, 8821

[vi] Ksander G. M.; Yuan A. M.; Diefenbacher C. G.; Stanton J. L. *J. Med. Chem*. 1985, 28, 1606

[vii] The key feature of the structural assignment was a comparison of the NMR spectra with that of CBZ-glutamic acid. The chemical shift of the methine proton in the less polar compound was significantly different from the methine proton in CBZ-glutamic acid whereas in the more polar compound the significant difference was in the methylene protons.

[viii] It was not possible to analyse (HPLC or NMR) the anhydride for the presence of the diastereomer to demonstrate the absence of racemisation during the DCC mediated ring closure reaction.

[ix] The anhydride of menthyloxycarbonyl-(S)-glutamic acid was subjected to a similar series of reactions. Comparison with the similar products from the enantiomeric acid allowed the four possible products to be assigned unambiguously on the HPLC trace.

[x] King J. F.; du Manoir J. R.; *J. Am. Chem. Soc.* 1975 97 2566

[xi] Two minor by-products are observed.

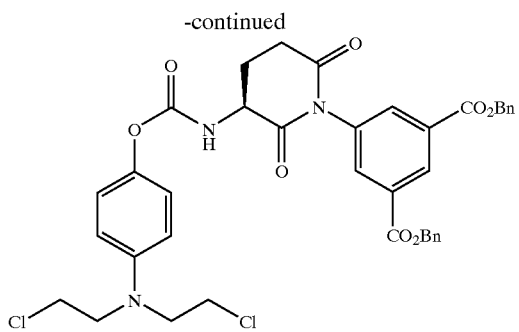

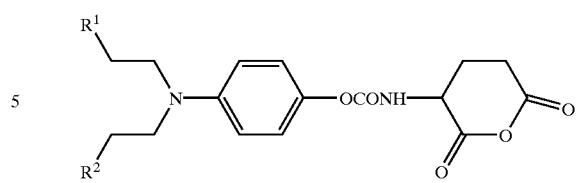

with a compound of Formula III:

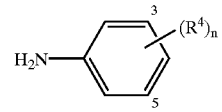

to give a compound of Formula I and optionally further comprising deprotecting $R^4$ and optionally converting the product thus obtained into a pharmaceutically acceptable salt thereof.

2. A method according to claim 1 in which $R^1$ and $R^2$ are chloro, $R^3$ is a alphamethylbenzylamine salt of carboxylic acid, n is 2 and $R^4$ is a protected form of COOH.

3. A method according to claim 2 wherein $R^4$ is COOBn.

4. A method according to claim 3 wherein $R^4$ is attached to the 3 and 5 positions of the phenyl ring.

5. A method according to claim 4 wherein the asterisked chiral carbon in Formula I has S configuration.

6. A method according to any one claims 1–5 wherein the reaction is performed in the presence of DMAP(4-dimethylaminopyridine).

7. A method according to claim 6 wherein the reaction is performed at a temperature of −40 to 0°.

8. A method according to claim 7 wherein the reaction is performed at a temperature of −35 to −25°.

9. A compound of Formula I:

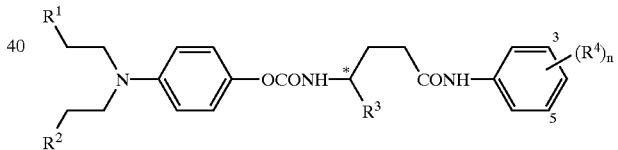

in which $R^1$ and $R^2$ are chloro, $R^3$ is an alphamethylbenzylamine salt of carboxylic acid, $(R^4)_n$ represents a benzyl protected 3,5-dicarboxylic acid and the asterisked chiral carbon in Formula I has S configuration.

10. A compound according to claim 9 in crystalline form wherein said alphamethylbenzylamine is in enantiomerically pure (R)- or (S)-configuration.

*xii* A crystalline product was also obtained in about the same isolated yield with (R)-α-methylbenzylamine. It was noticed that the two diastereomeric salts did crystallise at significantly different rates from the same solvent mixture but it is not known which salt would be more useful in further work on enhancing the purity of the derived ZD9063P.

*xiii* A sample of the regioisomeric Dibenzyl Ester was isolated by chromatography and its structure confirmed by NMR. Removal of the benzyl ester groups gave a compound very closely related to, but clearly different from, ZD9063P by HPLC and NMR analysis.

*xiv* AN—area normalised

*xv* Analysis by chiral HPLC using a CHI-DMB column, solvent system iso-hexane/isopropanol/TFA (75/25/0.1), flow 1 mL/min and detection at 254λ.

*xvi,xvii* Residual toluene and THF were detected in both spectra.

What is claimed is:

1. A method of preparation of a compound of Formula I or an $R^4$ deprotected derivative thereof:

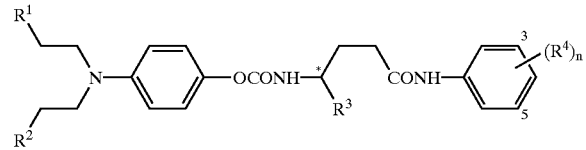

wherein $R^1$ and $R^2$ independently represent chloro, bromo, iodo or $OSO_2Me$;

$R^3$ represents COOH or a salt of carboxylic acid;

n is 1, 2, 3 or 4;

$R^4$ represents a protected form of COOH, tetrazol-5-yl or $SO_3H$; and in which the method comprises reacting a compound of Formula II:

* * * * *